(12) United States Patent
Lee et al.

(10) Patent No.: US 12,357,752 B2
(45) Date of Patent: Jul. 15, 2025

(54) IV FLOW REGULATOR

(71) Applicant: SUNGWON MEDICAL CO., LTD, Chungcheongbuk-do (KR)

(72) Inventors: Dae Hee Lee, Chungcheongbuk-do (KR); Hyun Chan Jo, Chungcheongbuk-do (KR); Sang Won Jo, Chungcheongbuk-do (KR); Seung Hong Baek, Chungcheongbuk-do (KR)

(73) Assignee: SUNGWON MEDICAL CO., LTD, Chungcheongbuk-Do (KR)

( * ) Notice: Subject to any disclaimer, the term of this patent is extended or adjusted under 35 U.S.C. 154(b) by 607 days.

(21) Appl. No.: 17/706,708

(22) Filed: Mar. 29, 2022

(65) Prior Publication Data

US 2022/0305198 A1 Sep. 29, 2022

(30) Foreign Application Priority Data

Mar. 29, 2021 (KR) ........................ 10-2021-0040758

(51) Int. Cl.
*A61M 5/168* (2006.01)

(52) U.S. Cl.
CPC .... *A61M 5/16881* (2013.01); *A61M 5/16813* (2013.01); *A61M 2206/20* (2013.01)

(58) Field of Classification Search
CPC .......... A61M 5/16804; A61M 5/16881; A61M 5/16813; A61M 39/26
See application file for complete search history.

(56) References Cited

FOREIGN PATENT DOCUMENTS

| KR | 20110115931 A | * | 10/2011 |
| KR | 101837519 B1 | * | 3/2018 |

* cited by examiner

*Primary Examiner* — Nilay J Shah
(74) *Attorney, Agent, or Firm* — Harness, Dickey & Pierce, P.L.C.

(57) ABSTRACT

There is provided an IV flow regulator, which includes an upper lever; a lower lever which is disposed below the upper lever and regulates the flow rate of the IV by a regulation operation of rotating by facing the upper lever; a cover fastened to the lower lever; and switching restraint unit which switches a restraint state in which the cover and the lower lever are mutually restrained to enable the regulation operation and a free state in which the cover and the lower lever are not mutually restrained to disable the regulation operation, according to a relative position of the cover and the lower lever.

2 Claims, 8 Drawing Sheets

1100

1200

1421

1411

1300

IV FLOW REGULATOR

CROSS-REFERENCE TO RELATED APPLICATIONS

This application claims the priority of Korean Patent Application No. 10-2021-0040758 filed on Mar. 29, 2021, in the Korean Intellectual Property Office, the disclosure of which is incorporated herein by reference.

FIELD

The present disclosure relates to an IV flow regulator, and more particularly, to an IV flow regulator capable of selecting a state in which the IV may be regulated and a state in which the IV may not be regulated by adjusting a displacing position of a cover, which may be confirmed from the outside.

BACKGROUND

This section provides background information related to the present disclosure which is not necessarily prior art.

An intravenous (IV) set currently on the market uses a roller clamp or a flow rate regulator to regulate the amount of IV supplied per unit time.

The roller clamp controls the IV flow rate by pressing or releasing a tube to which the IV is supplied to limit the cross-sectional area of the tube. There are advantages of a simple structure and an easy operation, but there is a problem that precise control of the flow rate is difficult and a change in flow rate due to carelessness may be large.

The IV flow rate is determined by the diagnosis of a medical professional, but when the IV flow rate is excessively high, serious conditions such as shock may be caused. Accordingly, the unintended change in the IV flow rate is recognized as a fatal problem as a medical device.

A device for regulating an IV flow rate introduced to solve the problem is an IV flow regulator consisting of an upper lever and a lower lever that are disposed in parallel in a direction of the IV tube to be coupled to each other.

By rotating the upper and lower levers facing each other with the same rotational shaft, the IV flow regulator of regulating the flow rate of the IV enables more precise flow rate control compared to the roller clamp.

In particular, since the flow rate is regulated only by a regulation operation of rotating the upper lever and the lower lever to face each other with both hands, there is stability that a possibility of an unintended flow rate change situation is significantly lowered compared to the roller clamp.

However, even in such an IV flow regulator, there is still a problem of illegal manipulation by a third party other than medical professionals, such as curious children or patients

SUMMARY

An aspect of the present disclosure provides an IV flow regulator capable of preventing an unintended change in IV flow rate.

This section provides a general summary of the disclosure and is not a comprehensive disclosure of its full scope or all of its features.

According to an aspect of the present disclosure, there is provided an IV flow regulator including an upper lever; a lower lever which is disposed below the upper lever and regulates the flow rate of the IV by a regulation operation of rotating by facing the upper lever; a cover fastened to the lower lever; and switching restraint unit which switches a restraint state in which the cover and the lower lever are mutually restrained to enable the regulation operation and a free state in which the cover and the lower lever are not mutually restrained to disable the regulation operation, according to a relative position of the cover and the lower lever.

In the IV flow regulator according to an aspect of the present disclosure, the cover may accommodate the lower lever therein and slide up and down to be switched between the restraint state and the free state.

In the IV flow regulator according to an aspect of the present disclosure, the switching restraint unit may include a switching unit that maintains the restraint state and the free state; and a restraining unit that mutually restrains the lower lever and the cover.

In the IV flow regulator according to an aspect of the present disclosure, the state switching unit and the lever restraining unit may be projected or depressed on the outer surface of the lower lever and the inner surface of the cover, respectively, to be fitted to each other.

In the IV flow regulator according to an aspect of the present disclosure, in the free state, the cover may completely cover the lower lever so that the lower lever is not able to be gripped by the hand.

In the IV flow regulator according to an aspect of the present disclosure, the cover may be made of a transparent material to confirm the shape of the outer surface of the lower lever and the shape of the inner surface of the cover.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION

Hereinafter, exemplary embodiments for implementing an IV flow regulator according to the present disclosure will be described in detail with reference to the accompanying drawings.

However, exemplary embodiments of the intrinsic technical spirit of the present disclosure may not be limited to exemplary embodiments to be described below, and cover the range that may be easily proposed by substituting or changing the exemplary embodiments to be described below by those skilled in the art based on the intrinsic technical spirit of the present disclosure.

Further, since terms used below are selected for easy description, the terms are not limited to dictionary meanings and should be appropriately interpreted as meanings consistent with the technical spirit of the present disclosure in order to grasp the intrinsic technical spirit of the present disclosure.

Figure 1:
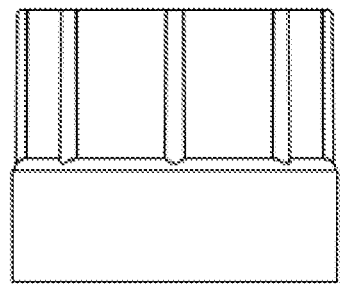
FIG. 1 is a front view illustrating a first exemplary embodiment of an IV flow regulator according to the present disclosure.
Figure 1:
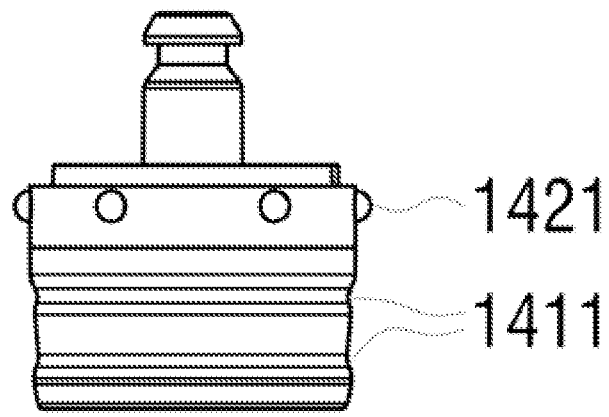
Figure 1:
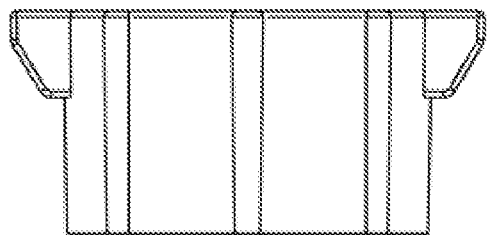

FIG. 1 is a front view illustrating a first exemplary embodiment of an IV flow regulator according to the present disclosure, in which an upper lever, a lower lever, and a cover are separated from each other.

Figure 2:
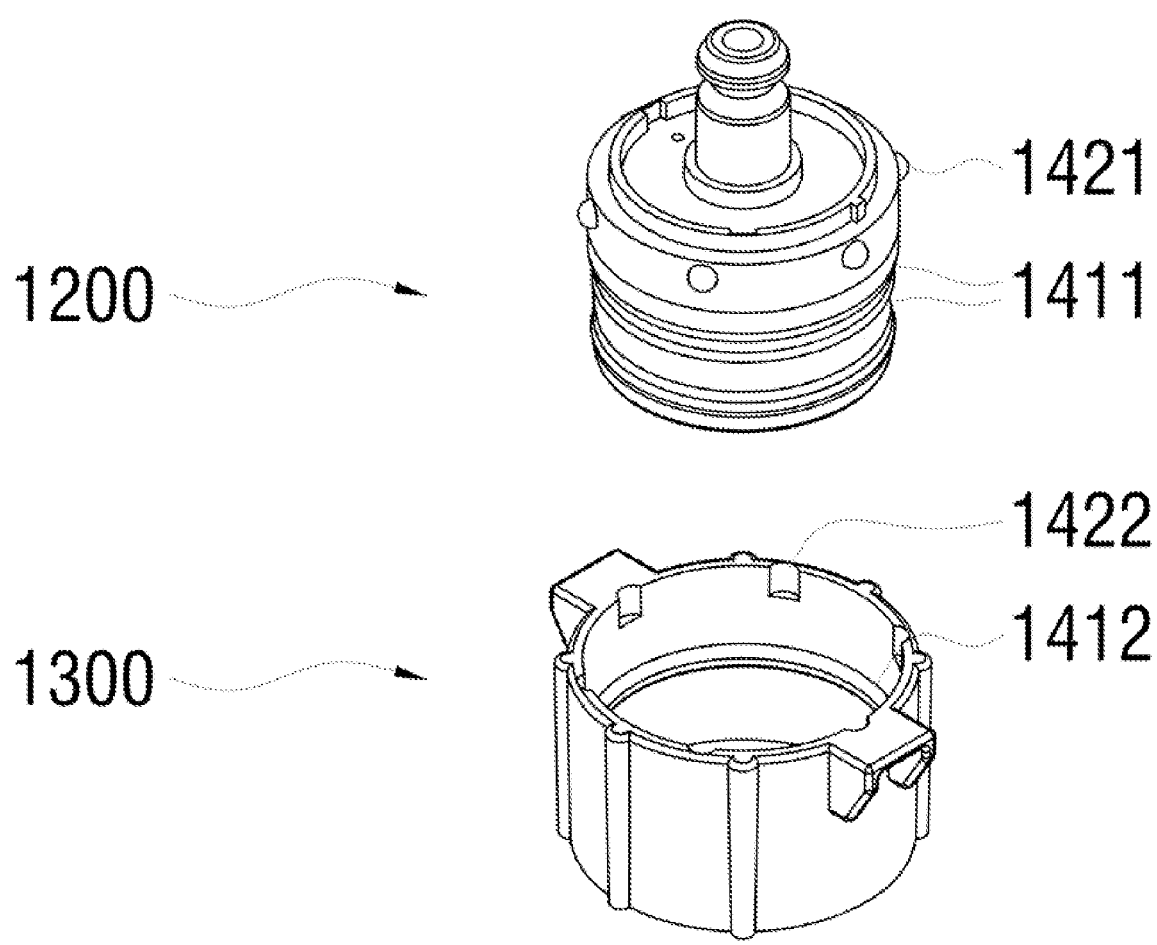
FIG. 2 is a perspective view of a lower lever and a cover in FIG. 1.
Figure 3:
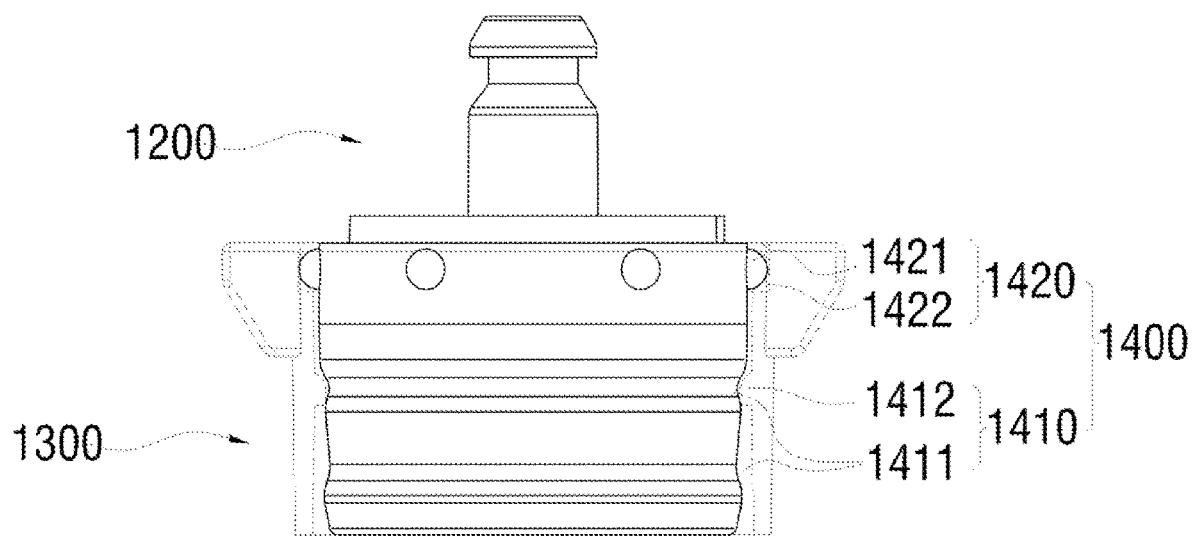
FIG. 3 is a front view for describing a restraint state of the IV flow regulator of FIG. 1.
Figure 4:
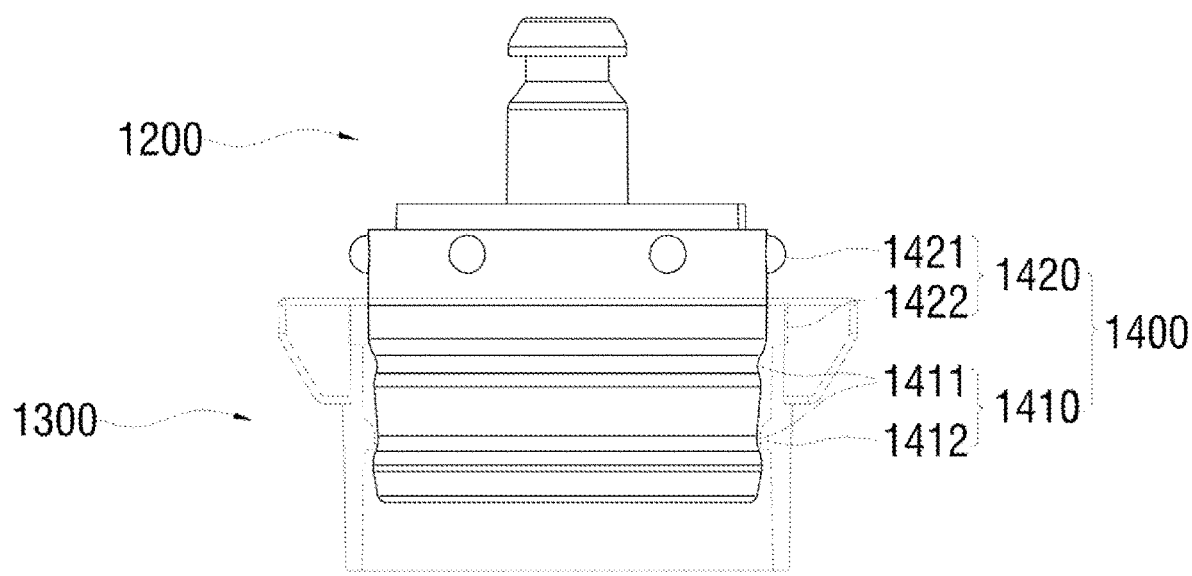
FIG. 4 is a front view for describing a free state of the IV flow regulator of FIG. 1.

FIG. 2 is a perspective view of a lower lever and a cover in FIG. 1, FIG. 3 is a front view for describing a restraint state of the IV flow regulator of FIG. 1, and FIG. 4 is a front view for describing a free state of the IV flow regulator of FIG. 1.

Referring to FIGS. 1 to 4, an IV flow regulator according to the exemplary embodiment includes an upper lever 1100, a lower lever 1200, a cover 1300, and a switching restraint unit 1400.

The upper lever 1100 is disposed on the upstream side of a tube to which an IV is supplied.

The lower lever 1200 is disposed below the upper lever 1100, that is, on the downstream side of the tube to which the IV is supplied. The flow rate of the IV is regulated by a regulation operation of rotating the lower lever 1200 facing the upper lever 1100.

The generation of a path through which the IV moves through the upper lever 1100 and the lower lever 1200 by the internal structure and regulation operation of the upper lever 1100 has already been widely used, and thus, a detailed description thereof will be omitted.

The cover 1300 is fastened to the lower lever 1200.

The switching restraint unit 1400 switches a restraint state and a free state according to a relative position of the cover 1300 and the lower lever 1200.

In the restraint state, the cover 1300 and the lower lever 1200 are mutually restrained to enable the regulation operation, and in the free state, the cover 1300 and the lower lever 1200 are not mutually restrained to disable the regulation operation.

Accordingly, the IV flow regulator according to the exemplary embodiment may change the position of the cover 1300 to switch a state in which the regulation operation is enabled and a state in which the regulation operation is disabled.

In the state in which the regulation operation is disabled, since the cover 1300 freely rotates around the outer circumferential surface of the lower lever, the regulation operation is disabled.

In the IV flow regulator according to the exemplary embodiment, the cover 1300 accommodates the lower lever 1200 therein and slides up and down to be switched between the restraint state and the free state.

The switching restraint unit 1400 includes a switching unit 1410 and a restraining unit 1420.

The switching unit 1410 maintains the selected restraint state and free state.

The restraining unit 1420 mutually restrains the lower lever 1200 and the cover 1300 in the above-described regulation operation direction, and thus, when the cover 1300 is gripped and rotated, the lower lever 1200 rotates.

In addition, the switching unit 1410 and the restraining unit 1420 are projected or depressed on the outer surface of the lower lever 1200 and the inner surface of the cover 1300, respectively, to be fitted to each other.

The switching unit 1410 may include a switching projection 1412 and a switching depression 1411, and the restraining unit 1420 may include a restraining projection 1421 and a restraining depression 1422.

In the IV flow regulator according to the exemplary embodiment, the switching projection 1412 is formed on the inner circumferential surface of the cover, and a pair of switching depressions 1411 is formed on the outer circumferential surface of the lower lever 1200 in upper and lower sides.

When the cover 1300 slides upward and the switching projection 1412 is fitted to the switching depression 1411 on the upper side, the restraint state is maintained, and when the cover 1300 slides downward and the switching projection 1412 is fitted to the switching depression 1411 on the lower side, the free state is maintained.

Accordingly, the IV flow regulator according to the exemplary embodiment may select the restraint state by sliding the cover 1300 upward, and on the contrary, may select the free state by sliding the cover 1300 downward.

In addition, the restraining projection 1421 is formed along an outer circumferential surface adjacent to an upper end of the lower lever 1200, and the restraining depression 1422 is formed along an inner circumferential surface adjacent to an upper end of the cover 1300.

Figure 5:
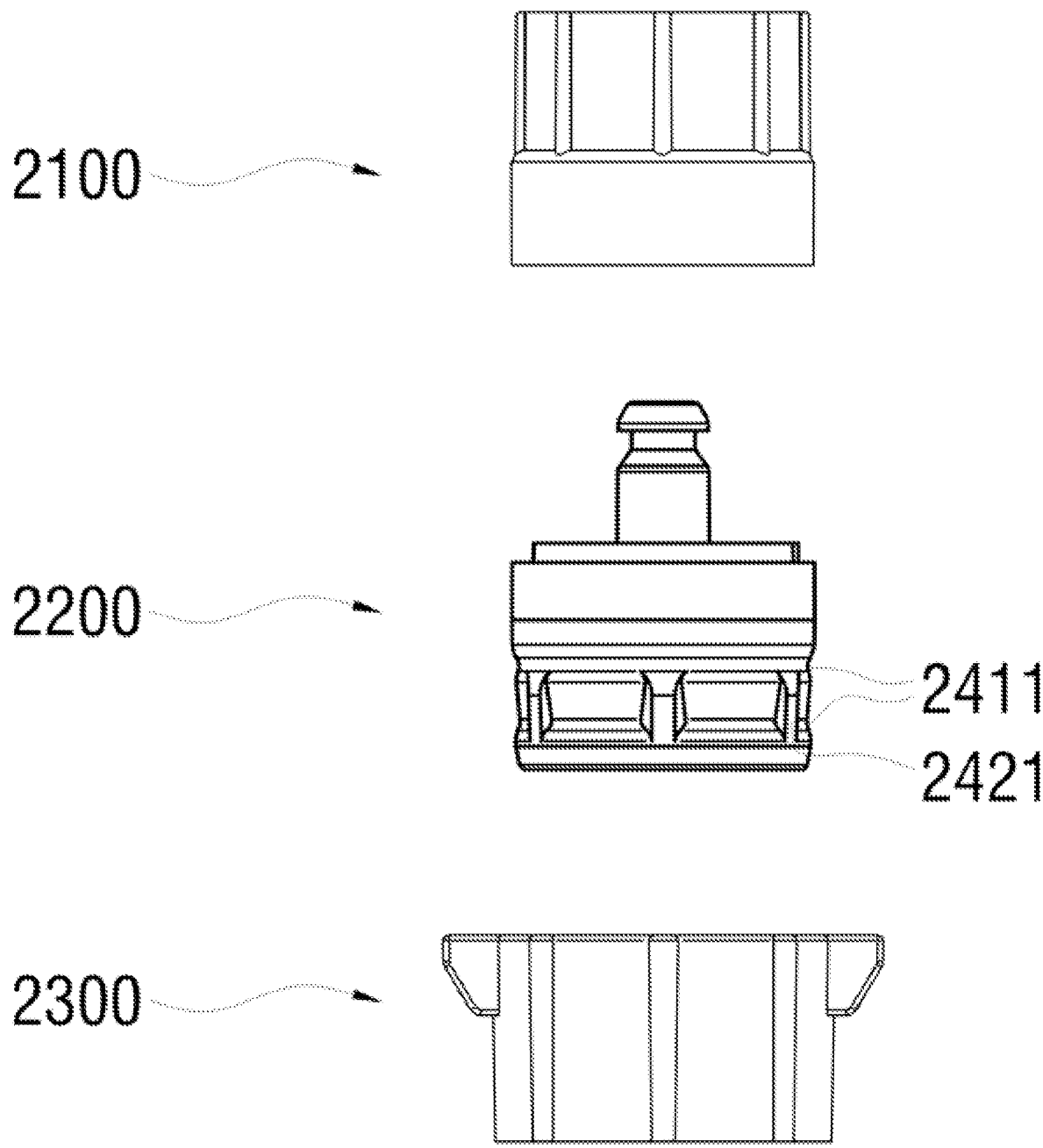
FIG. 5 is a front view illustrating a second exemplary embodiment of an IV flow regulator according to the present disclosure.

FIG. 5 is a front view illustrating a second exemplary embodiment of an IV flow regulator according to the present disclosure, in which an upper lever, a lower lever, and a cover are separated from each other.

Figure 6:
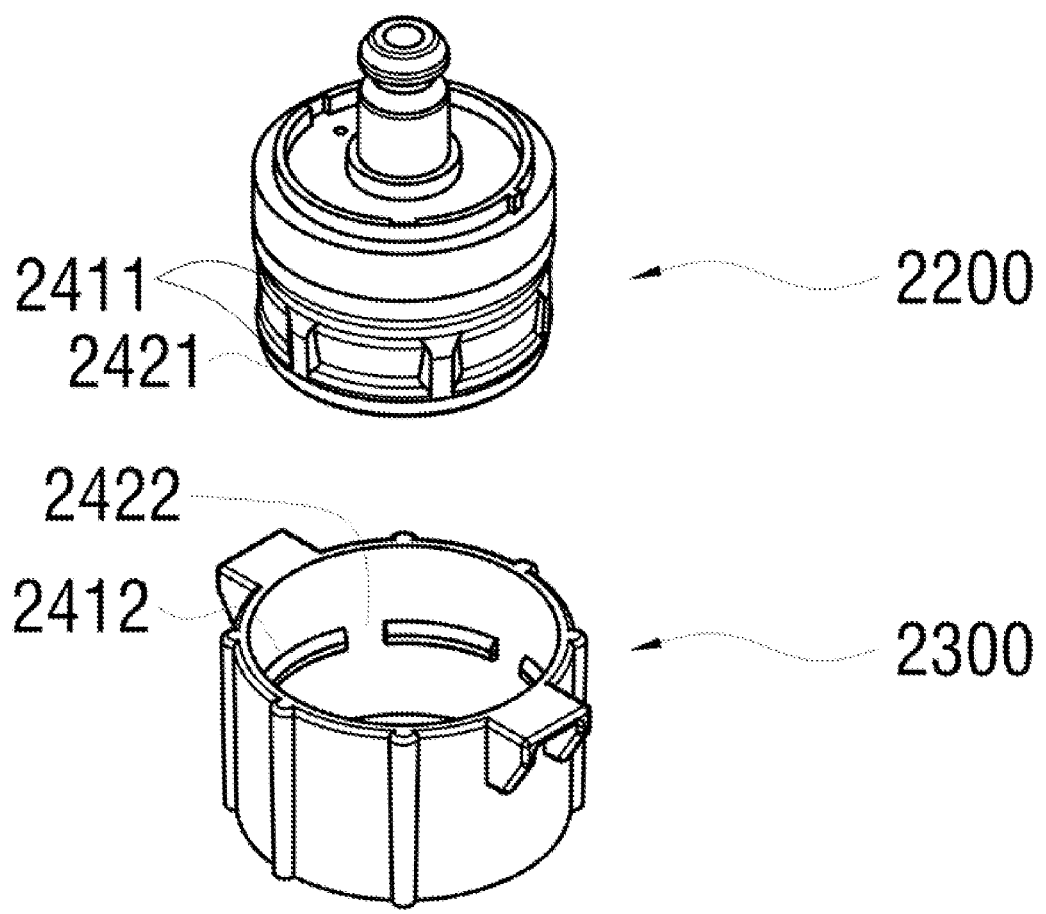
FIG. 6 is a perspective view of a lower lever and a cover in FIG. 5.
Figure 7:
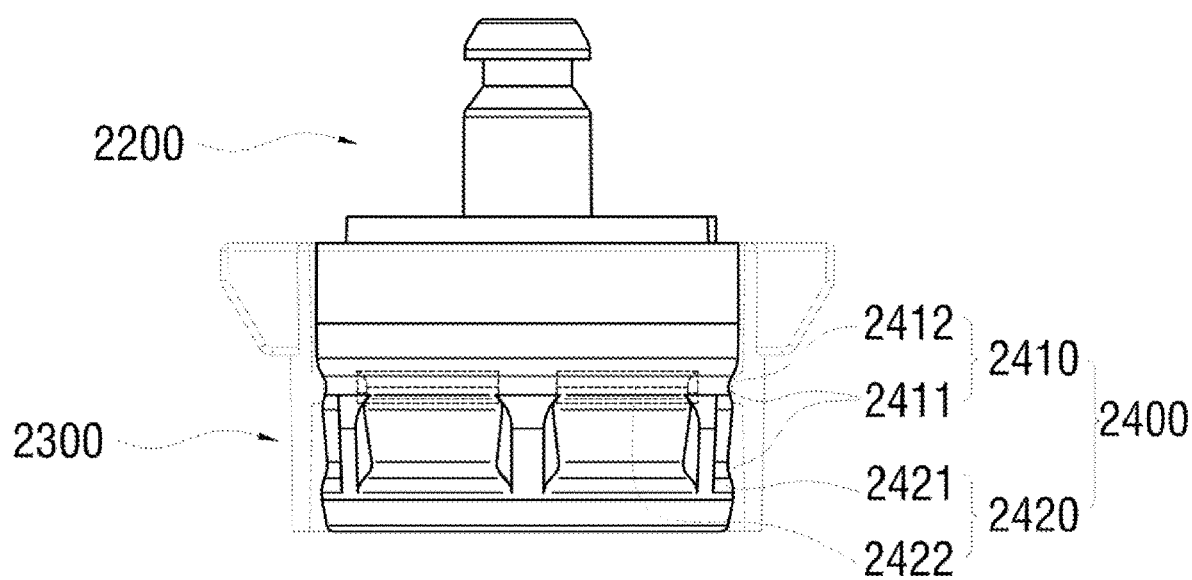
FIG. 7 is a front view for describing a restraint state of the IV flow regulator of FIG. 5.
Figure 8:
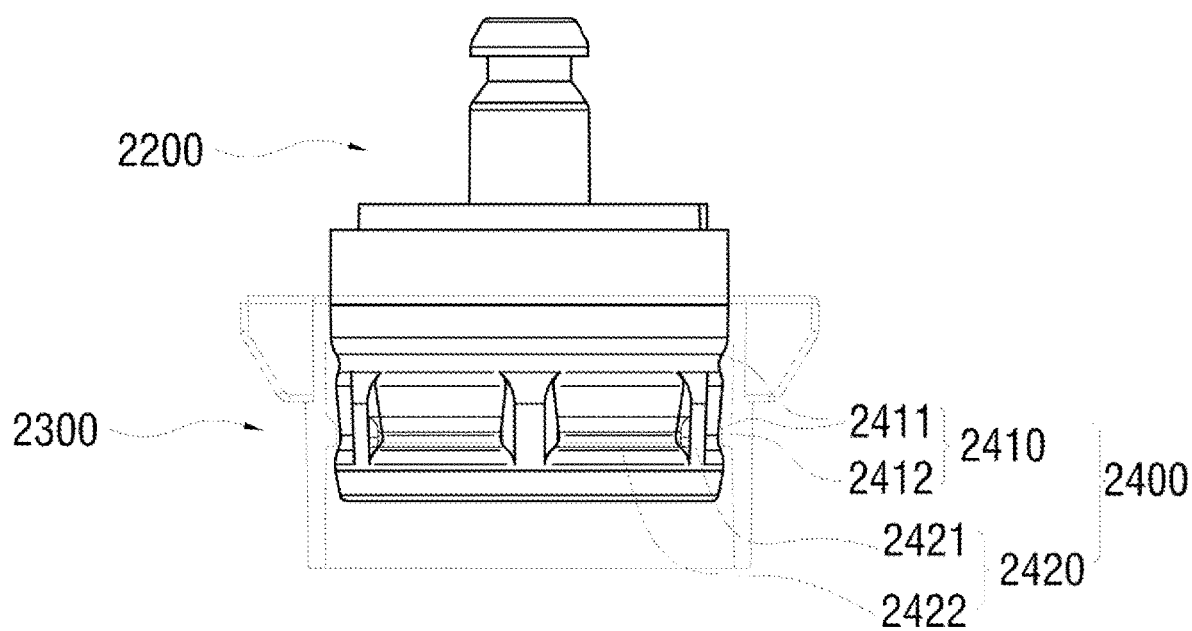
FIG. 8 is a front view for describing a free state of the IV flow regulator of FIG. 5.

FIG. 6 is a perspective view of a lower lever and a cover in FIG. 5, FIG. 7 is a front view for describing a restraint state of the IV flow regulator of FIG. 5, and FIG. 8 is a front view for describing a free state of the IV flow regulator of FIG. 5.

Referring to FIGS. 5 to 8, an IV flow regulator according to the exemplary embodiment includes an upper lever 2100, a lower lever 2200, a cover 2300, and a switching restraint unit 2400.

The upper lever 2100 is disposed on the upstream side of a tube to which an IV is supplied.

The lower lever 2200 is disposed below the upper lever 2100, that is, on the downstream side of the tube to which the IV is supplied. The flow rate of the IV is regulated by the regulation operation of rotating the lower lever 2200 facing the upper lever 2100.

The cover 2300 is fastened to the lower lever 2200.

The switching restraint unit 2400 switches a restraint state and a free state according to a relative position of the cover 2300 and the lower lever 2200.

In the restraint state, the cover 2300 and the lower lever 2200 are mutually restrained to enable the regulation operation, and in the free state, the cover 2300 and the lower lever 2200 are not mutually restrained to disable the regulation operation.

Accordingly, the IV flow regulator according to the exemplary embodiment may change the position of the cover 2300 to switch a state in which the regulation operation is enabled and a state in which the regulation operation is disabled.

In the state in which the regulation operation is disabled, since the cover 2300 freely rotates around the outer circumferential surface of the lower lever 2200, the regulation operation is disabled.

In the IV flow regulator according to the exemplary embodiment, the cover 2300 accommodates the lower lever 2200 therein and slides up and down to be switched between the restraint state and the free state.

The switching restraint unit 2400 includes a switching unit 2410 and a restraining unit 2420.

The switching unit 2410 maintains the selected restraint state and free state.

The restraining unit 2420 mutually restrains the lower lever 2200 and the cover 2300 in the above-described regulation operation direction, and thus, when the cover 2300 is gripped and rotated, the lower lever 2200 rotates.

In addition, the switching unit 2410 and the restraining unit 2420 are projected or depressed on the outer surface of the lower lever 2200 and the inner surface of the cover 2300, respectively, to be fitted to each other.

The switching unit 2410 may include a switching projection 2412 and a switching depression 2411, and the restraining unit 2420 may include a restraining projection 2421 and a restraining depression 2422.

In the IV flow regulator according to the exemplary embodiment, the switching projection 2412 is formed on the inner circumferential surface of the cover 2300, and a pair of switching depressions 2411 is formed on the outer circumferential surface of the lower lever 2200 in upper and lower sides.

When the cover 2300 slides downward and the switching projection 2412 is fitted to the switching depression 2411 on the lower side, the restraint state is maintained, and when the cover 2300 slides upward and the switching projection 2412 is fitted to the switching depression 2411 on the upper side, the free state is maintained.

Accordingly, the IV flow regulator according to the exemplary embodiment may select the restraint state by sliding the cover 2300 downward, and on the contrary, may select the free state by sliding the cover 2300 upward.

At this time, the restraining projection 2421 is formed in the lower switching depression 2411 of the lower lever 2200, and the restraining depression 2422 is formed along the switching projection 2412.

That is, in the IV flow regulator according to the exemplary embodiment, the restraining projection 2421 and the restraining depression 2422 are formed along the switching projection 2412 and the switching depression 2411.

In addition, in the IV flow regulator according to the exemplary embodiment, in the free state, the cover 2300 completely covers the lower lever 2200, so that the lower lever 2200 may not be gripped by the hand.

Accordingly, since the lower lever 2200 is not exposed to the outside in the free state, the regulation operation may be completely blocked.

At this time, the cover 2300 is formed of a transparent material to confirm the shape of the outer surface of the lower lever 2200 and the shape of the inner surface of the cover 2300.

The switching restraint unit 2400 according to the exemplary embodiment is disposed at a position fully covered by the cover 2300. Accordingly, the positions of the restraining projection 2421 and the restraining depression 2422 may not be confirmed.

By using the cover 2300 formed of the transparent material, it is possible to move the cover 2300 by aligning the positions of the restraining projection 2421 and the restraining depression 2422 when switched from the free state to the restraint state.

As set forth above, according to exemplary embodiments of the invention, the cover covering the lower lever is used to select a restraint state of regulating the flow rate of the IV and a free state of not regulating the flow rate, thereby preventing a change in flow rate of the IV due to carelessness and easily confirming the restraint state and the free state.

While the present invention has been shown and described in connection with the exemplary embodiments, it will be apparent to those skilled in the art that modifications and variations can be made without departing from the spirit and scope of the invention as defined by the appended claims.

What is claimed is:

1. An intravenous (IV) flow regulator comprising:
   an upper lever;
   a lower lever which is disposed below the upper lever and regulates a flow rate of an IV by a regulation operation of rotating by facing the upper lever;
   a cover fastened to the lower lever; and
   a switching restraint unit which switches a restraint state in which the cover and the lower lever are mutually restrained to enable the regulation operation and a free state in which the cover and the lower lever are not mutually restrained to disable the regulation operation, according to a relative position of the cover and the lower lever;
   wherein the cover accommodates the lower lever therein and slides up and down to be switched between the restraint state and the free state;
   wherein the switching restraint unit includes a state switching unit that maintains the restraint state and the free state; and a lever restraining unit that mutually restrains the lower lever and the cover;
   wherein the state switching unit and the lever restraining unit are projected or depressed on an outer surface of the lower lever and an inner surface of the cover, respectively, to be fitted to each other; and
   wherein in the free state, the cover completely covers the lower lever so that the lower lever is not able to be gripped by a hand.

2. The IV flow regulator of claim 1, wherein the cover is made of a transparent material to confirm a shape of the outer surface of the lower lever and a shape of the inner surface of the cover.

\* \* \* \* \*